US007838280B2

(12) United States Patent
Shvabsky et al.

(10) Patent No.: US 7,838,280 B2
(45) Date of Patent: Nov. 23, 2010

(54) DEVICE FOR SQUEEZING OF BIOLOGICAL MASS OF CULTURES

(76) Inventors: Oleg Shvabsky, 2500 Parkview Dr. #2518, Hallandale Beach, FL (US) 33009; Jacob Gitman, 1111 Kane Concourse #518, Bay Harbor Island, FL (US) 33154

( * ) Notice: Subject to any disclaimer, the term of this patent is extended or adjusted under 35 U.S.C. 154(b) by 0 days.

(21) Appl. No.: 12/380,802

(22) Filed: Mar. 4, 2009

(65) Prior Publication Data

US 2010/0227391 A1    Sep. 9, 2010

(51) Int. Cl.
*C12M 1/00*    (2006.01)
*B30B 1/00*    (2006.01)

(52) U.S. Cl. .................... 435/283.1; 100/171; 100/176; 100/179; 100/223

(58) Field of Classification Search .............. 435/283.1, 435/289.1, 325, 379; 210/401, 402, 217, 210/326, 352; 100/176, 171, 179, 223; 99/557; 492/33

See application file for complete search history.

(56) References Cited

U.S. PATENT DOCUMENTS 3,927,680 A * 12/1975 Stefan et al. ................. 460/128
4,917,009 A *  4/1990 Edo ............................ 100/118

* cited by examiner

*Primary Examiner*—William H Beisner
*Assistant Examiner*—Danielle Henkel
(74) *Attorney, Agent, or Firm*—I. Zborovsky

(57) ABSTRACT

A device for wringing a biological mass of cultures has a substantially vertical container having a bottom provided with a discharge opening, a rotor means located under the discharge opening and including at least two rotors which are rotatable toward one another to receive a biological mass therebetween, wherein the rotors are provided with a plurality of substantially radially extending plungers which are displaceable in a radial direction.

5 Claims, 4 Drawing Sheets

DEVICE FOR SQUEEZING OF BIOLOGICAL MASS OF CULTURES

BACKGROUND OF THE INVENTION

The present invention relates to devices for separation of two fractions, namely a biological mass of a culture, in particular an agriculture, and water.

The separation of these fractions is usually prepared by a centrifugal method or a milling method. A centrifugal machine is expensive equipment and consumes a lot of energy. While mills do not provide high quality squeezing of the biological mass.

It is believed to be advisable to provide an improved device for wringing of biological mass of cultures.

SUMMARY OF THE INVENTION

Accordingly, it is an object of the present invention to provide a device for squeezing of biological mass of cultures, which avoids the disadvantages of the prior art.

In keeping with these objects and with others which will become apparent hereinafter, one feature of the present invention resides, briefly stated, in a device for squeezing a biological mass of cultures, comprising a substantially vertical container having a bottom provided with a discharge opening; a rotor means located under said discharge opening and including at least two rotors which are rotatable toward one another to receive a biological mass therebetween, wherein said rotors are provided with a plurality of substantially radially extending plungers which are displaceable in a radial direction.

Another feature of the present invention resides, briefly stated, in springs applying a spring action toward said plungers.

A further feature of the present invention resides, briefly stated, in said hopper has a bottom with a shape substantially corresponding an outer shape of said rotors.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
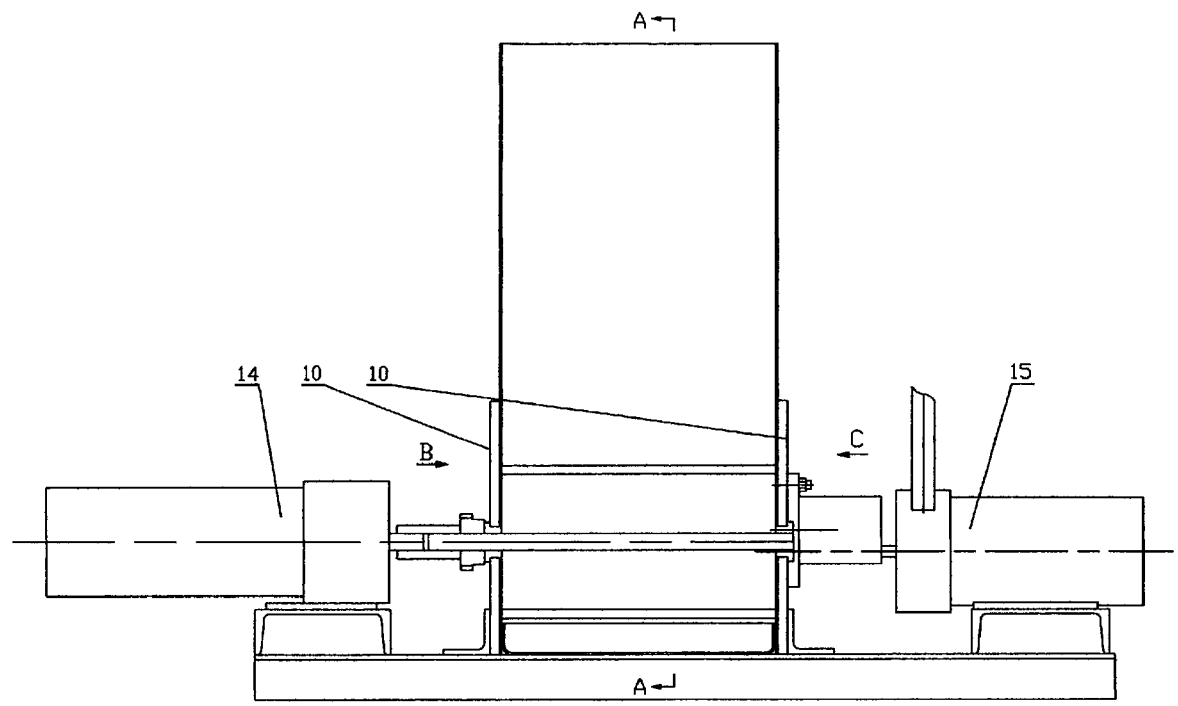
FIG. 1 is a view showing a device for squeezing of biological mass of cultures.
Figure 2:
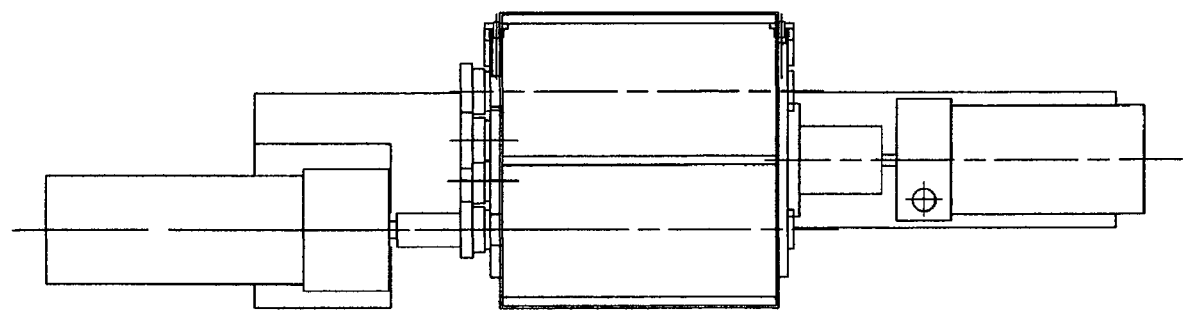
FIG. 2 is a plan view of the inventive device for squeezing of biological mass of cultures.
Figure 4:
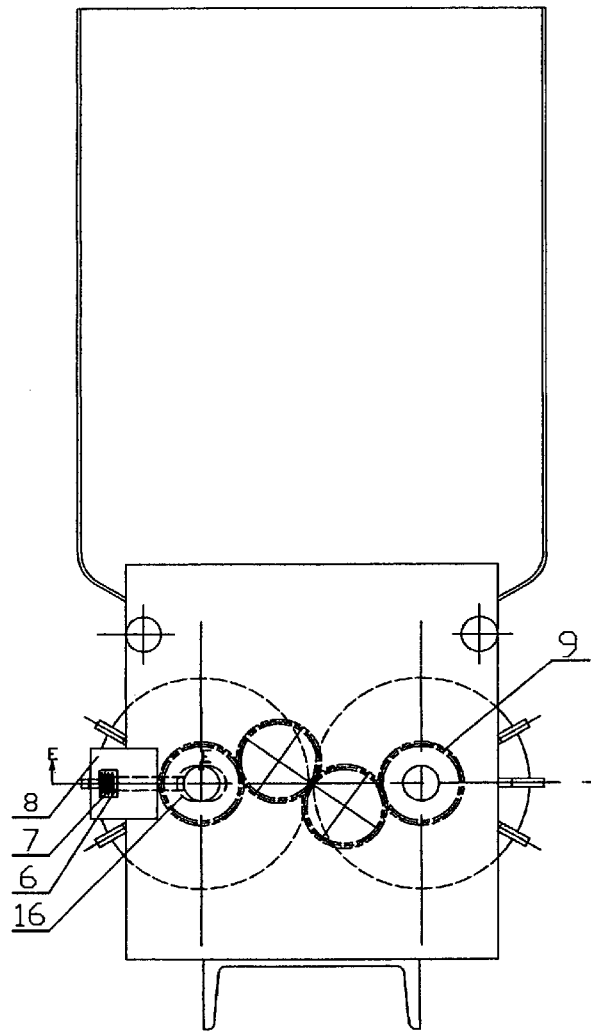
FIG. 4 is a view as seen in direction of an arrow II of the inventive device.

A device for squeezing of biological mass of cultures includes a hopper which is identified with reference numeral 1 and has a bottom narrowing downwardly. A part of the bottom has a shape providing a contact with a wringing unit and ending in a slot for discharge of a solution of a culture. Two supports are identified by 10.

The device further has two rotors 2. The rotors are provided with movable plungers 3 and flat springs 4.

End sides of the rotors are provided with limiting rings 5, gear set 9, a pressing rod 6, a spring 7, a regulator 8 of spring tension, a filtering device 12, a receiving device 13 for filtered water, a vessel for collecting of squeezed culture 11, a row-speed electric motor 14, and a centrifugal group 15.

The device for squeezing of biological mass of cultures operates in the following manner. A solution of a biological mass is supplied for example from a reactor in which the biomass has been grown, into the hopper 1, and through a slot in its lower part is supplied into a closed space between the lines of contact of the plungers 3, a bottom of the bunker 1, ends of casing supports 10.

The outer surfaces of the plunger provide a linear contact. The plungers 3 are located in the rotors and, under the action of the plate spring 4, abutting against the ring 5, assume positions which are spaced from the center by a maximum distance. In response to the contact against a bottom of the hopper during contact with the bottom of the hopper, and with each other their perform a reciprocating motion and more along the slots of the rotor.

Figure 3:
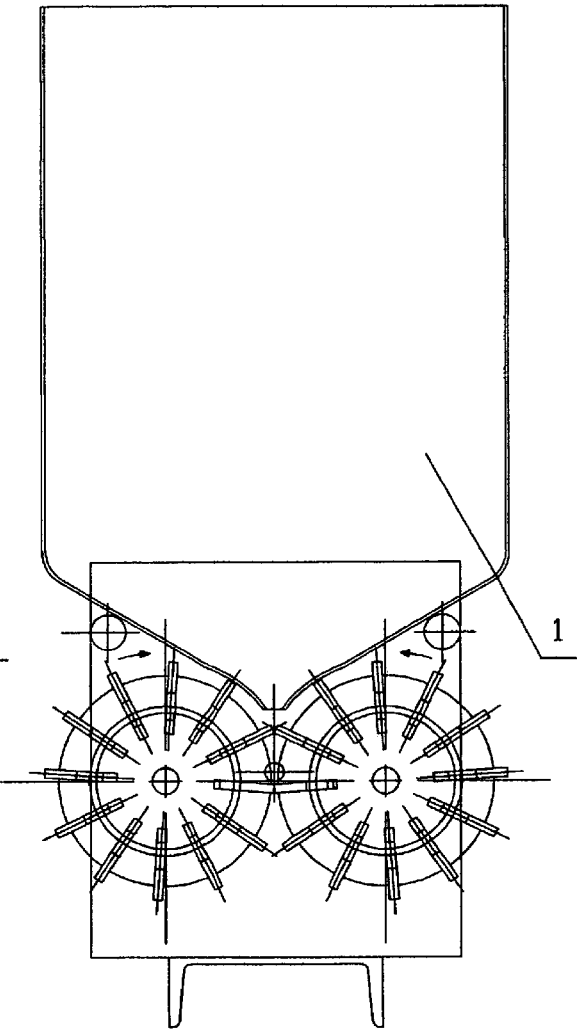
FIG. 3 is a view showing a section I-I of the inventive device through rotors of the device.
Figure 7:
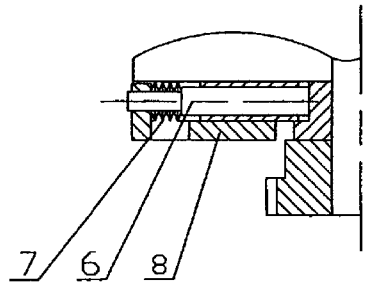
FIG. 7 is a view showing a section E-E of pulling device.
Figure 6:
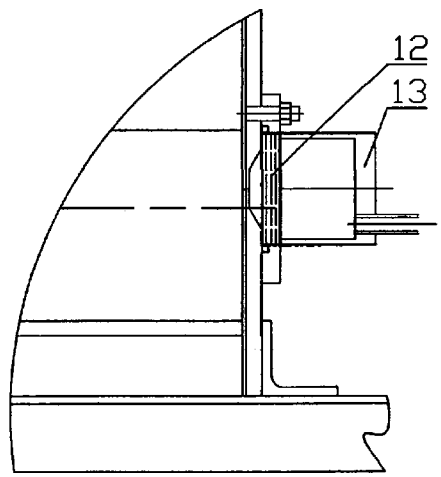
FIG. 6 is a view showing a section IV-IV through a filtering unit of the inventive device.
Figure 5:
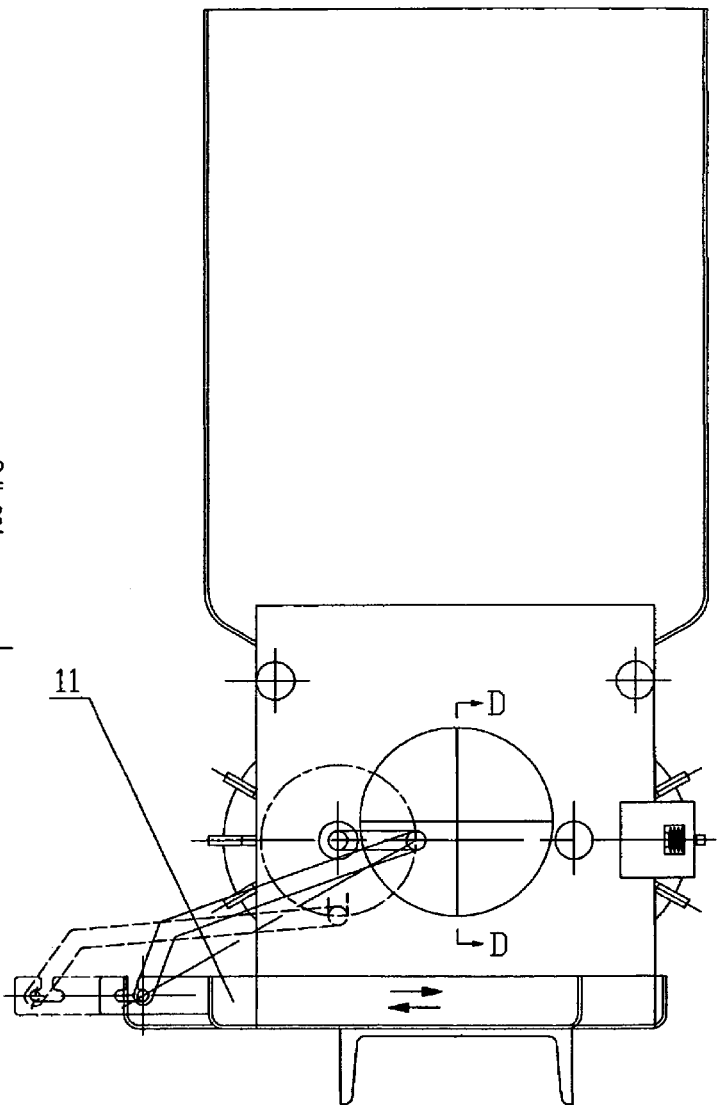
FIG. 5 is a view as seen in direction of arrow III of the inventive device.
Figure 8:
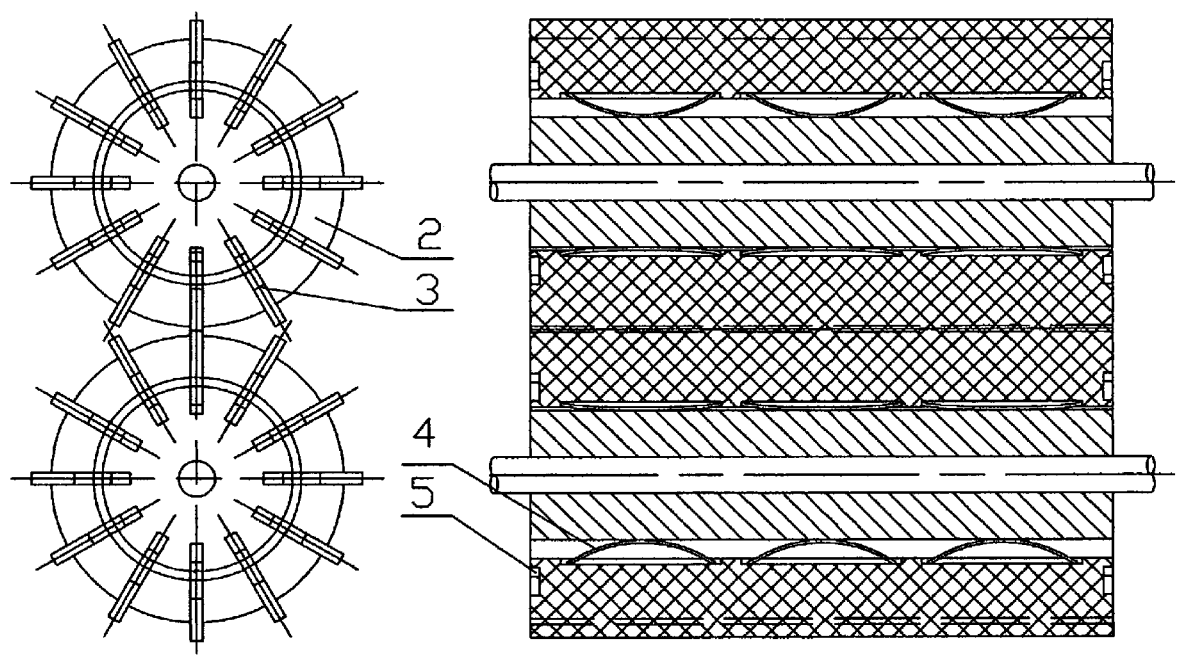
FIG. 8 is a view showing the rotors of the inventive device for squeezing of biological mass of cultures.

The rotation of the rotors 2 is provided by the electric motor 11 with the gears 9 toward one another along the arrows shown in FIG. 3, and the central gears move with the contract of 16a water medium passes through the filter 12 and is removed from the biomass. It is supplied into the receiving device 13, then by the pump 15 is pumped to a vessel (not shown) for use in a cycle of bioreactor for growing the biomass. Fractions with biomass, as a denser structure, are displaced by the plungers 3, squeezed by the rotors 2, pressed into the vessel 11, which reciprocates for uniform placement of collected product, and then it is supplied to a further operations. The force necessary for squeezing of the biomass is provided by the pull regulator 8, which compresses the springs 11 and through the red transfers it to the axis of the rotor.

It will be understood that each of the elements described above, or two or more together, may also find a useful application in other types of constructions differing from the type described above.

While the invention has been illustrated and described as embodied in a device for wringing of biological mass of cultures, it is not intended to be limited to the details shown, since various modifications and structural changes may be made without departing in any way from the spirit of the present invention.

Without further analysis, the foregoing will so fully reveal the gist of the present invention that others can, be applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for wringing a biological mass of cultures, comprising a substantially vertical container having a bottom with a hopper provided with a discharge opening; a rotor means located under said discharge opening of said hopper and including at least two rotors which have cylindrical surfaces and are rotatable toward one another to receive a biological mass therebetween, wherein said rotors are provided with a plurality of substantially radially extending plungers which reciprocate in slots in said rotors in a radial direction and are brought in contact with each other during rotation of the rotors.

2. A device as defined in claim 1; and further comprising springs applying spring action to said plungers to spring-bias said plungers radially outwardly.

3. A device as defined in claim 1, wherein said hopper has a bottom with a shape substantially corresponding to an outer shape of said rotors.

4. A device as defined in claim 1, wherein said container further comprising filtering means for filtering a liquid-exiting the device (6).

5. A device as defined in claim 1, further comprising means for driving said rotors in rotation, and including an electric motor and gear transmission between said electric motor and said rotors.

* * * * *